(12) United States Patent
Clement

(10) Patent No.: US 6,443,920 B1
(45) Date of Patent: Sep. 3, 2002

(54) PROTECTIVE ENCLOSURE FOR BODY SUPPORT

(76) Inventor: Margarita Clement, 17537 Blythe St., Northridge, CA (US) 91325

( * ) Notice: Subject to any disclaimer, the term of this patent is extended or adjusted under 35 U.S.C. 154(b) by 0 days.

(21) Appl. No.: 09/063,985

(22) Filed: Apr. 21, 1998

(51) Int. Cl.$^7$ ................................................ A61F 13/00
(52) U.S. Cl. .............................. 602/62; 602/60; 602/61
(58) Field of Search .................................. 602/5, 19, 23, 602/24, 60, 61, 62, 63, 79; 128/882; 2/455, 456, 465, 466

(56) References Cited

U.S. PATENT DOCUMENTS

| | | | | |
|---|---|---|---|---|
| 2,531,757 A | * | 11/1950 | Whinery | 602/79 |
| 4,084,586 A | * | 4/1978 | Hettick | 602/60 |
| 4,474,573 A | * | 10/1984 | Detty | 602/26 |
| 4,709,692 A | * | 12/1987 | Kirchenberg et al. | 602/19 |
| 4,832,010 A | * | 5/1989 | Lerman | 602/63 |
| 4,926,845 A | * | 5/1990 | Harris | 602/19 |
| 4,977,898 A | * | 12/1990 | Hunt | 602/61 |
| 5,423,852 A | * | 6/1995 | Daneshvar | 606/201 |
| 5,425,702 A | * | 6/1995 | Carn et al. | 602/62 |
| 5,595,192 A | * | 1/1997 | Tatum | 128/869 |
| 5,706,523 A | * | 1/1998 | Witzel | 2/238 |
| 5,779,658 A | * | 7/1998 | Saca | 602/61 |

* cited by examiner

Primary Examiner—Kim M. Lewis

(57) ABSTRACT

A soft, flexible, low friction enclosing device designed to function as a protective support for the human body when lying in bed or on other horizontal surfaces. A support wrap (10) is made of sturdy, flame-retardant low friction material such as nylon for durability and for ease of moving enclosed patient along the surface of a bed or chair. An inner lining made of soft and pliable composite material such as foam rubber is enveloped by the support wrap (10). Velcro latches (30, 40) at predetermined locations provide means for attachment when the support is closed around the body.

5 Claims, 2 Drawing Sheets

PROTECTIVE ENCLOSURE FOR BODY SUPPORT

FIELD OF INVENTION

This invention relates to a protective device of soft, pliable material designed to provide cushioning for bedridden patients, with particular attention to hip, buttock, and lower extremity pressure points.

BACKGROUND OF THE INVENTION

For cushioning and protective purposes, it is already well known to utilize pull-on and soft-wrap support devices to protect elbows and knees from abrasion, and to restrict movement of inflamed joints.

As intended, these devices prevent bruising from falls, and ease pain from swollen joints. However, patients have been unable to find protective support devices to prevent bed sores, or Decubitis (localized areas of inflammation or deterioration of skin and subcutaneous tissues produced by pressure points).

Although knee and elbow supports provide some protection to those specific areas, they are relatively useless in cases involving bedridden or immobile persons suffering Decubitis. They do not provide therapeutic relief to pressure exerted on the skin between bony prominences, e.g. hips and the surface on which the body rests (mattress, examination table, etc.).

Currently, physicians order a topical medication and pads for the affected areas. However, these dressings cover only the inflamed spots while failing to prevent similar skin breakdown elsewhere on the body. The present invention provides protection to the hip, buttock, and lower extremities in the form of a formable, soft, pliable cushion of a predetermined configuration and prevent irritation such as bed sores caused by movement or rotation of the patient for purposes of comfort or administering personal hygiene.

SUMMARY OF THE INVENTION

Empirical studies and prior literature provide sufficient evidence to conclude that Decubitis, bed sores, and inflamed tissue pose serious problems to persons confined to bed for prolonged periods or whose incapacitation prevents voluntary movement.

The problem arises from (a) contact with firm bed mattresses or wheelchair seats and (b) infrequent rotation of the patient for long periods. In most cases, the breakdown of skin occurs in the area of bony prominences at the hip and the buttocks where there is insufficient subcutaneous cushion tissue, and, to a lesser extent, the upper back or shoulders where the body makes contact with the bed.

While physicians order topical medication and pads for the affected areas, these dressings cover only those inflamed spots while failing to prevent similar ulcerated points elsewhere. The enclosing body support of the invention will protect areas of the lower torso and extremities vulnerable to Decubitis.

The design of my invention allows for the placement of the individual on the device while it is open and in a flat configuration. The support is simply closed with adjustable Velcro latches, which facilitates proper fit and comfort. It also is designed to provide an opening for urination or catheterization. For purposes of bathing or personal hygiene, the Velcro latches are released and the enclosure is opened to allow free access to the patient without discomfort.

The objects and advantages of the flexible support wrap of the present invention are:

(a) to relieve or remove pressure to the skin from bony prominences of the hip and buttock areas;

(b) to stimulate circulation for bedridden persons unable to move frequently;

(c) to keep the skin protected from abrasive materials such as starched sheets and mattress covers and the residual laundry chemicals left on the sheets, etc.;

Further objects and advantages are to provide that the protective enclosing device be easily and conveniently opened and closed with minimal discomfort to the patient, which can increase muscular, skin and vascular tone through unrestricted blood circulation. Among other advantages, the present invention eliminates the need for rubber rings or doughnuts that merely increase the pressure around bony prominences.

In brief, the present invention provides an enclosure to protect bedridden patients from bed sores and skin breakdown, and to provide relief from the pain and discomfort from existing inflammation.

BRIEF DESCRIPTION OF THE DRAWINGS

The present invention will be better understood by reference to the drawing wherein.

DETAILED DESCRIPTION

Figure 1:
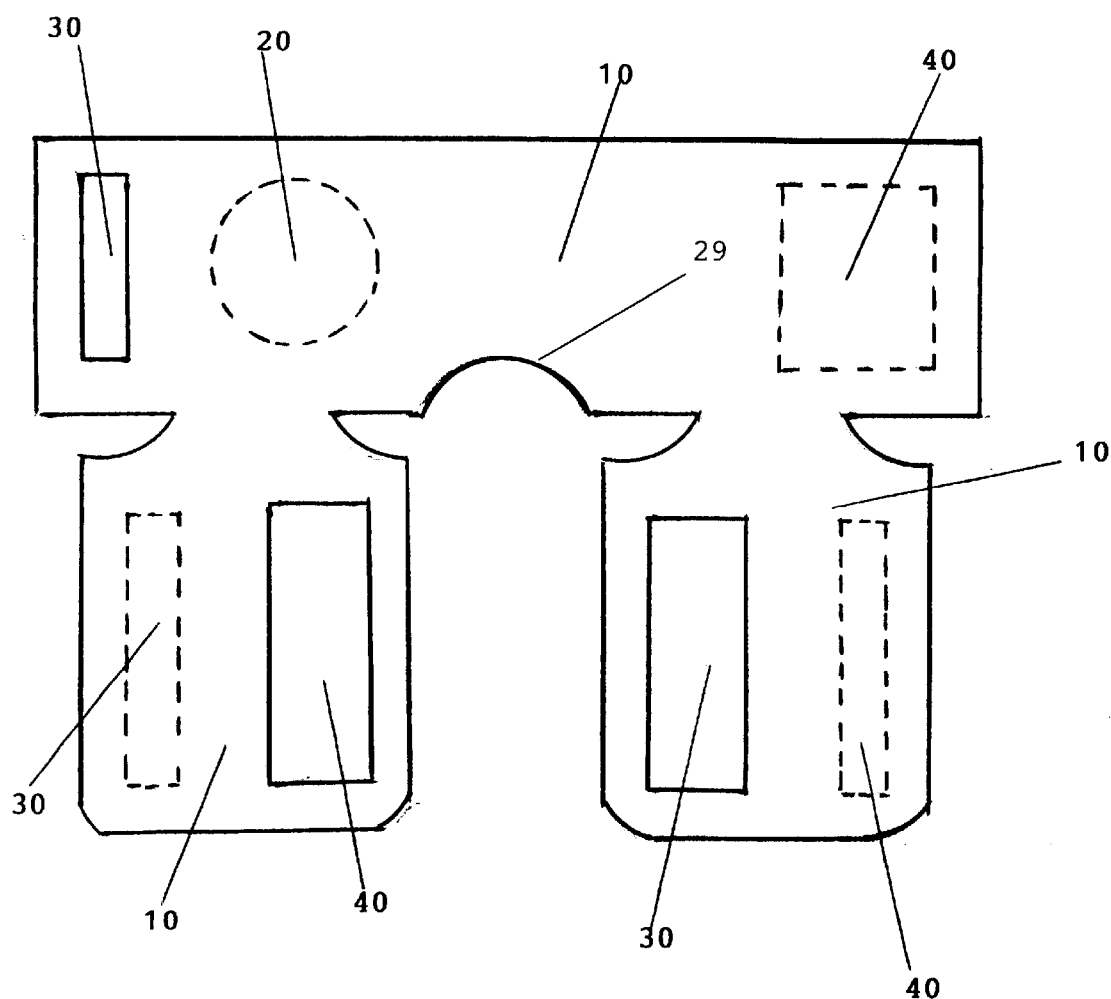
FIG. 1 is a plan view of the support wrap 10 according to the present invention while open, showing the location of detachable extra padding to protect the bony prominences of hip, buttock, and lower extremities.

A preferred embodiment of the present invention is illustrated in FIG. 1. The enclosing device has an outer or foundation portion 10 of a sturdy, flame-retardant, low-friction material such as nylon to facilitate easier movement on a bed surface by reducing drag friction. Nylon, rayon and Dacron are suitable low-friction materials that are also moisture-resistant and will retard the absorption of any body fluids from the patient. Additionally, this material is also flame-retardant in accordance with both OSHA and local safety regulations.

Velcro latches or fasteners 30 and 40 are attached to the support wrap to facilitate opening and closing the device as well as allow for adjustment to body size and patient comfort.

One or more detachable pads 20 is also provided to be attached on the support wrap 10 at locations of the body where extra padding is needed to further cushion bony prominences of the patient.

Figure 2:
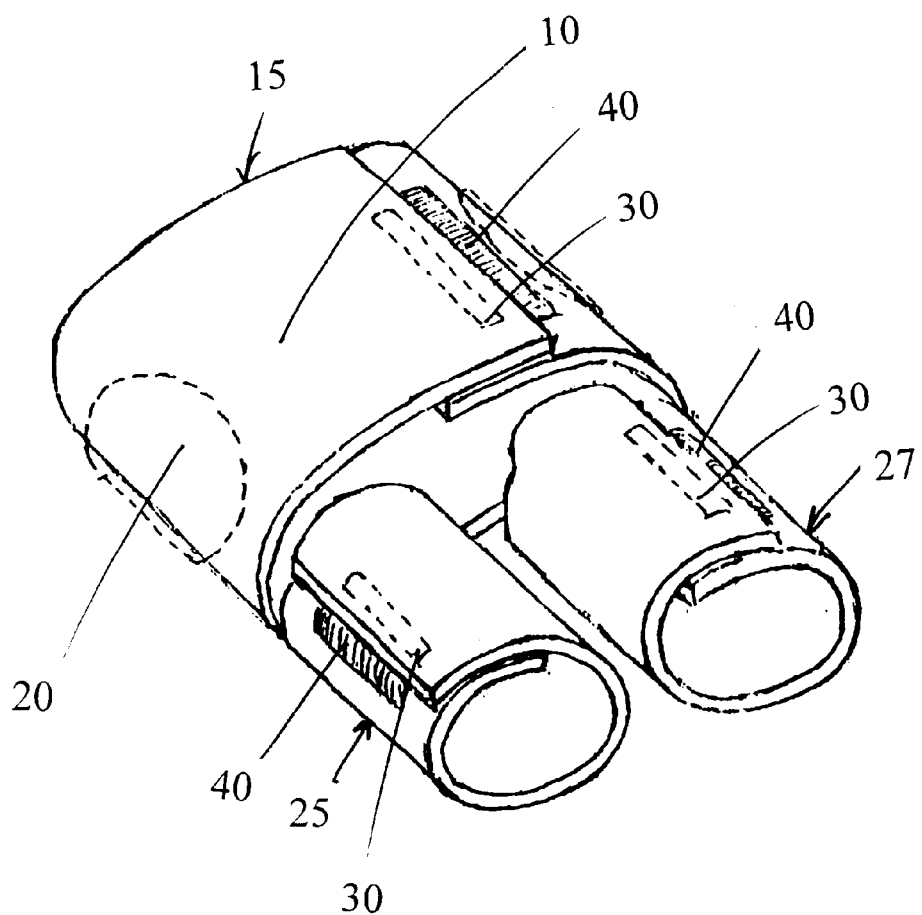
FIG. 2 is a perspective view showing the support wrap as it would appear when wrapped around a patient's body, cushioning bony prominences of the torso, hips and upper portions of the legs.

A perspective view of the present invention is shown in FIG. 2, illustrating the support wrap as it appears when closed around a patient's body. Velcro closures or fasteners 30, 40 allow the device to be closed as firmly or as loosely as comfort dictates.

The Velcro latch comprises a hook tape 30 and a loop tape 40. Loop tape 40 is made larger in width than tape 30 to permit adjustability and thereby fit the support wrap to the correct size for the patient The dimensions of the present invention will vary with the size of the patient: small, medium, and large. The dimensions also accommodate variations in accordance with sex, age, and body measurements.

The outer support wrap 10 serves as an envelope for an inner lining 12 of a softer material such as a composite foam rubber. The inner lining 12 is soft and pliable, providing a cushioning effect to prevent hard contact between the patient's bony prominences and bed or chair surfaces, and to allow inflamed areas of the patient's body to breathe and benefit from the increase in blood circulation which is permitted to existing skin lesions or bed sores.

Further advantages of the protective enclosure and body support wrap 10 include:

(a) a bedridden or wheelchair-bound patient will be relieved of pain and discomfort caused by hard contact with mattresses and seats.

(b) the cushioning effect will prevent development of inflamed tissue around bony prominences and allow the curative effect of increased blood circulation to existing lesions or bed sores (Decubitis).

(c) the Velcro fasteners will permit quick and easy opening and closing of the device for purposes of bathing, changing undergarments, personal hygiene, and application of topical medication or new dressings.

The manner of using the protective enclosure and body support is simple and convenient for the attending health care provider or family member. The patient is placed on the opened device so that the lower body portion of the patient's torso is placed on the upper portion 15 of the support wrap. The patient is centered on portion 15 with the buttocks situated along the lower portion 15 and the legs overlying the lower portions 25, 27 of the support wrap. The support wrap 10 is then closed and covers the body from waist area to the knees with the inner lining protecting and cushioning the hips bony prominences, buttocks, and upper parts of the legs and at the same time a cutout 29 permits catherization and urination.

When the wrap is closed, the device is held in place on the patient's body by the Velcro latches 30 and 40, adjusted for body size and patient comfort. Opening the device is equally simple and easy by pulling the Velcro hook tape 30 and loop tape 40 apart to free the overlapping edges of the support.

Because the low friction exterior material of the wrap 10 does not create drag friction with the bed surface, the support wrap can be easily slid out from under the patient if removal is desired.

The present invention thus protects and supports the body easily and conveniently, can be closed and reopened as often as needed as treatment or hygiene requires, and can be removed without discomfort to the individual. The invention thus relieves pressure on skin and subcutaneous tissue; prevents sensory loss, or absence of the patient's awareness of pain and pressure; permits the supply of nutrients to tissue cells, thus avoiding edema, by improved blood circulation which, in turn, aids the healing of existing ulcers or bed sores; and facilitates increased activity by the patient because the device reduces or eliminates the discomfort of motion, allowing activity to thereby increase muscular, skin, and vascular tone.

Although the descriptions above refers to certain specifics, these should not be construed as limiting the scope of the invention. The protective body support will also prevent exacerbation of dermatological anomalies attributable to bacterial and viral infection, such as HIV/AIDS.

What is claimed is:

1. A protective enclosure body support to provide cushioning for a patient's body from waist to knee, comprising:

(a) an enclosing cloth support wrap of a predetermined configuration;

(b) an inner lining of a soft pliable foam rubber material enveloped by the support wrap to cushion critical areas of the body;

(c) at least one auxiliary padding for detachable engagement with the body support in predetermined locations to provide additional cushioning for the support; and (d) a plurality of fasteners placed at predetermined locations on the support wrap to permit the closure of the flexible protective support wrap to permit the closure of the flexible protective support wrap around the target areas body; the predetermined configuration of the support wrap having an upper portion of a size to enclose the lower torso of the patient's body when the free ends are overlapped and a pair of lower portions of a size to enclose each leg of the patient's body when the free ends are overlapped.

2. A body support according to claim 1 wherein the enclosing support wrap is fabricated of a low friction material.

3. A body support according to claim 2 where the material is selected from the group consisting of nylon, rayon and Dacron.

4. A body support according to claim 2 wherein the fasteners are a plurality of Velcro fasteners, each having a hook tape and a loop tape of a predetermined size.

5. A body support according to claim 4 wherein the loop tape is larger than the hook tape to permit adjustment of the size of the support, when it is wrapped around a patient's body.

\* \* \* \* \*